United States Patent
James

(10) Patent No.: US 6,294,548 B1
(45) Date of Patent: *Sep. 25, 2001

(54) MULTIDOSE VIAL FORMULATIONS FOR ADMINISTERING ENDO-N-(9-METHYL-9-AZABICYCLO[3.3.1]NON-3-YL)-1-METHYL-1H-INDAZOLE-3-CARBOXAMIDE HYDROCHLORIDE

(75) Inventor: Susan James, Haverhill (GB)

(73) Assignee: Hoffmann-La Roche Inc., Nutley, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/548,838

(22) Filed: Apr. 13, 2000

Related U.S. Application Data

(63) Continuation of application No. 09/304,894, filed on May 4, 1999.
(60) Provisional application No. 60/084,110, filed on May 4, 1998.

(51) Int. Cl.$^7$ ................................................. A61K 31/44
(52) U.S. Cl. ........................................... 514/299; 514/872
(58) Field of Search ..................................... 514/299, 872

(56) References Cited

U.S. PATENT DOCUMENTS 4,886,808 * 12/1989 King ...................................... 514/299
5,225,407 * 7/1993 Oakley et al. ........................ 514/215

OTHER PUBLICATIONS

Remington: The Science and Practice of Pharmacy, Mack Publishing Co., Chapter 87, p. 1529, 1995.*

Ettinger, et al.; Cancer, vol. 78, No. 1, 1996, pp. 144–151.

Cassidy, et al.; Br. Journal of Cancer, vol. 58, 1988, pp. 651–653.

Carmichael, et al.; Cancer Chem. Pharm., vol. 24, 1989, pp. 45–49.

Allen, et al.; Eur. J. Clin. Pharm., vol. 46, 1994, pp. 159–162.

Allen, et al.; Eur. J., Clin. Pharm., vol. 48, 1995, pp. 519–520.

Addelman, et al., J. Clin. Oncology, vol. 8, No. 2, 1990, pp. 337–341.

Remington: The Science and Practice of Pharmacy, 1995, 19th edition, Chapter 87, pp. 1529.

* cited by examiner

Primary Examiner—Shep K. Rose
Assistant Examiner—Donna Jagoe
(74) Attorney, Agent, or Firm—George W. Johnston; Patricia S. Rocha-Tramaloni; Robert A. Silverman

(57) ABSTRACT

Invented are improved multidose aqueous formulations of endo-N-(9-methyl-9-azabicyclo[3.3.1.]non-3-yl)-1-methyl-1H-indazole-3-carboxamide hydrochloride.

10 Claims, No Drawings

MULTIDOSE VIAL FORMULATIONS FOR ADMINISTERING ENDO-N-(9-METHYL-9-AZABICYCLO[3.3.1]NON-3-YL)-1-METHYL-1H-INDAZOLE-3-CARBOXAMIDE HYDROCHLORIDE

This is a continuation of application Ser. No. 09/304,894 filed May 4, 1999, which claims benefit from U.S. Provisional Application No. 60/084,110, filed May 4, 1998.

This invention relates to improved formulations of endo-N-(9-methyl-9-azabicyclo[3.3.1.]non-3-yl)-1-methyl-1H-indazole-3-carboxamide hydrochloride.

The compound is represented by Structure I:

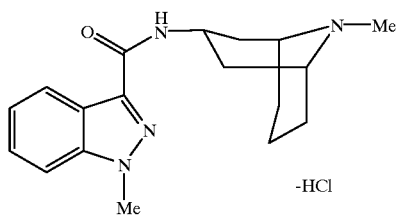

(I)

The formulations of this invention are useful as anti-emetics, particularly in the treatment of cytotoxic agent induced emesis.

DETAILED DESCRIPTION OF THE INVENTION

Endo-N-(9-methyl-9-azabicyclo[3.3.1.]non-3-yl)-1-methyl-1H-indazole-3-carboxanide hydrochloride is a compound which is disclosed and claimed, along with pharmaceutically acceptable salts, hydrates and solvates thereof, as being useful as an anti-emetic, particularly in the treatment of cytotoxic agent induced emesis, in U.S. Pat. No. 4,886,808, the entire disclosure of which is hereby incorporated by reference. Endo-N-(9-methyl-9-azabicyclo[3.3.1.]non-3-yl)-1-methyl-1H-indazole-3-carboxamide hydrochloride can be prepared by methods such as described in U.S. Pat. No. 4,886,808. Endo-N-(9-methyl-9-azabicyclo[3.3.1.]non-3-yl)-1-methyl-1H-indazole-3-carboxamide hydrochloride is commercially available under the trade name Kytril and is also known by the generically as granisetron hydrochloride.

As indicated in the *Physicians' Desk Reference®*, 1997 edition, published by Medical Economics Company, Inc. at Montvale, N.J., an injectable dosage form of endo-N-(9-methyl-9-azabicyclo[3.3.1.]non-3-yl)-1-methyl-1H-indazole-3-carboxamide hydrochloride is commercially available in a 1 ml single use vial containing an aqueous solution comprising 1.12 mg of granisetron hydrochloride equivalent to granisetron 1 mg. The recommended dosage for granisetron hydrochloride is 10 mcg/kg infused intravenously over 5 minutes, beginning within 30 minutes before initiation of chemotherapy.

All publications, including but not limited to patents and patent applications, cited in this specification are herein incorporated by reference as though fully set forth.

The prior 1 mg/ml single dose vial has proved undesirable in a number of ways. The recommended dose is 10 mcg/kg of body weight. Thus, the 1 ml vial is not ideal for patients weighing greater than 100 kg as a portion of a second vial will have to be utilized and the remaining medication discarded. Further, product wastage will occur when administering to lighter patients who do not require the full 1 ml dose. Numerous advantages would be realized if a suitable multidose vial comprising endo-N-(9-methyl-9-azabicyclo[3.3.1.]non-3-yl)-1-methyl-1H-indazole-3-carboxamide hydrochloride could be prepared. The advantages of a multidose vial of endo-N-(9-methyl-9-azabicyclo[3.3.1.]non-3-yl)-1-methyl-1H-indazole-3-carboxamide hydrochloride include: making weight-based dosing more efficient thereby minimizing wasted product, conserving resources, containing costs, making better use of storage space and more cost effective to produce and transport.

Numerous difficulties were encountered in preparing multidose aqueous formulations of endo-N-(9-methyl-9-azabicyclo[3.3.1.]non-3-yl)-1-methyl-1H-indazole-3-carboxanide hydrochloride. Included in the difficulties encountered is the need for and the selection of an antimicrobial preservative. Further, the multidose formulation experienced a shift in pH during the sterilization process. The pH of the solution was stabilized by the addition of a buffer. The previous single dose vial did not contain an antimicrobial preservative or a buffer.

The difficulties encountered in preparing multidose aqueous formulations of endo-N-(9-methyl-9-azabicyclo[3.3.1.]non-3-yl)-1-methyl-1H-indazole-3-carboxamide hydrochloride were over come and suitable multidose formulations prepared based on the Experimental data presented below.

All of the pharmaceutical excipients utilized herein are known and are commercially available. Before carrying out the Examples of the invention described herein, the test solutions were placed into glass vials and autoclaved for about 15 to 60 minutes at about 121° C. to provide sterile solutions.

The following examples further illustrate the present invention. The examples are not intended to limit the scope of the invention as defined hereinabove and as claimed below.

EXAMPLE 1

Selection of a Buffer

Endo-N-(9-methyl-9-azabicyclo[3.3.1.]non-3-yl)-1-methyl-1H-indazole-3-carboxamide hydrochloride is stable in solution over the pH range 2 to 7. In preparing multidose formulations for stability testing it was noted that a pH shift effect occasionally occurred. In order to stabilize the pH, a citrate buffer was added to control the pH of the solution to a target pH of 6 with limits of 5 to 7.

EXAMPLE 2

Selection of Preservatives for Evaluation

In order to select appropriate preservative systems for evaluation, a list of antimicrobial agents suitable for parenteral use were reviewed. The ideal preservative for the multidose vial formulation would meet the following criteria:

Stable and active over the pH range 5 to 7

Non-reactive with components of the container/closure system

Effective against a wide range of microorganisms

Stable during steam sterilization

Acceptability with the FDA

Widely used in products commercially available in the US

From a review of the literature, the following preservative systems were selected as possible preservatives for evaluation:

Meta-cresol (about 0.25%)

Benzyl alcohol (about 1.0%)

Methyl paraben (about 0.18%)

Propyl paraben (about 0.02%)

Methyl paraben (about 0.18%)+propyl paraben (about 0.02%)

In selecting these preservatives as potential candidates for the multidose formulations, it was noted that meta-cresol showed good efficacy against gram-positive and gram-negative bacteria, yeasts and molds over the pH range 5–7. Benzyl alcohol is commercially available and showed moderate efficacy against all four types of organism over the pH range 5 to 7. The parabens showed similar efficacy to benzyl alcohol. The concentrations selected correspond to levels typically used in commercially available parenteral products.

EXAMPLE 3

Stability of Preservatives During Autoclaving

The five preservative systems were assessed for stability to the autoclave process. Placebo solutions were prepared at pH6, filled into 2 ml glass vials and autoclaved for 15 and 60 minutes at 121° C. A cycle time of 60 minutes was selected to mimic the most extreme conditions to which a vial on the outside of a full autoclave load could be subjected to. Solutions were prepared at pH6 since this was the target pH of the multidose dose formulation. The early experiments were performed using 2 ml flint glass vials and West #1816 Teflon faced, bromobutyl rubber stopper.

The results in Table 1 show the meta-cresol and benzyl alcohol contents as a percentage of their initial values. Both benzyl alcohol and meta-cresol showed good stability with no change in preservative content after 60 minutes, hence they were selected for further evaluation.

Table 2 shows the results of the parabens systems. External standards of the parabens could not be prepared due to their poor aqueous solubility. The results were therefore determined by are normalization, whereby peak areas are expressed as a percentage of the total peak area of the chromatograph. The results indicate that all three parabens systems are unstable to autoclaving.

The preservative content of each solution decreased and an unknown peak on the HPLC chromatograph increased. The unknown peak was hypothesized to be the hydrolysis product, 40 hydroxy benzoic acid. Based on these results the parabens were rejected as possible preservatives.

TABLE 1

Stability of Preservative Systems t Autoclave: Meta-Cresol and Benzyl Alcohol

|  | Meta-Cresol (0.25%) | Benzyl Alcohol (1.0%) |
| --- | --- | --- |
| Initial content | 2.6 mg/ml | 10.0 mg/ml |
| Content after 15 mins (% of initial) | 100 | 100 |
| Contents after 60 mins (% of initial) | 100 | 100 |

TABLE 2

Stability of Preservative Systems to Autoclave: Parabens

|  | Methyl-Parabens (0.25%) | Propyl Parabens (0.02%) | Methyl Parabens + Propyl Parabens (0.18% + 0.02%) |
| --- | --- | --- | --- |
| Initial content | 99.8% (0.2%)* | 99.4% (0.6%)* | 88.0% + 11.7% (0.3%)* |
| Content at 15 mins | 96.3% (3.7%)* | 98.4% (1.6%)* | 85.7% + 11.5% (2.9%)* |
| Content at 60 mins | 93.5% (6.5%)* | 97.2% (2.7%)* | *83.0% + 11.0% (6.0%)* |

NOTE: The results are expressed as percentage of total peak area determined by area normalisation.
*Area percent for the unknown peak

EXAMPLE 4

Compatibility of endo-N-(9-methyl-9-azabicyclo[3.3.1.]non-3-yl)-1-methyl-1H-indazole-3-carboxamide hydrochloride with Preservatives The compatibility of endo-N-(9-methyl-9-azabicyclo[3.3.1.]non-3-yl)-1-methyl-1H-indazole-3-carboxamide hydrochloride with both benzyl alcohol and meta-cresol was investigated. Table 3 shows granisetron content, degradation products and preservative content for each formulation after 1 months' storage. Samples stored at 30° C. and 40° C. were compared to control samples retained at 5° C.

The benzyl alcohol formulation showed good stability at all storage conditions. No difference was seen in endo-N-(9-methyl-9-azabicyclo[3.3.1.]non-3-yl)-1-methyl-1H-indazole-3-carboxamide hydrochloride content, degradation products or benzyl alcohol content in comparison to the 5° C. controls.

The meta-cresol formulation showed no difference in endo-N-(9-methyl-9-azabicyclo[3.3.1.]non-3-yl)-1-methyl-1H-indazole-3-carboxamide hydrochloride content or meta-cresol content. However, samples at all three conditions contained 0.9% of a major degradation product, exceeding the product specification limit of 0.7%.

To investigate this phenomenon further, the stability during autoclaving experiment was repeated on samples of the meta-cresol formulation. Results for this experiment are presented in Table 4. The degradation product content increased from 0.05% before autoclaving to 0.53% at 15 minutes then 0.93% at 60 minutes. The results confirm that endo-N-(9-methyl-9-azabicyclo[3.3.1.]non-3-yl)-1-methyl-1H-indazole-3-carboxamide hydrochloride is incompatible with meta-cresol, which causes degradation of endo-N-(9-methyl-9-azabicyclo[3.3.1.]non-3-yl)-1-methyl-1H-indazole-3-carboxamide hydrochloride the autoclave cycle. Meta-cresol was therefore rejected as a possible preservative.

Benzyl alcohol was selected as the most appropriate preservative system.

TABLE 3

Compatibility of endo-N-(9-methyl-9-azabicyclo[3.3.1.]non-3-yl)-
1-methyl-1H-indazole-3-carboxamide hydrochloride with Preservatives

| Storage Condition | Preservative Content | Granisetron | degradation product 1 | degradation product 2 | degradation product 3 |
|---|---|---|---|---|---|
| Meta-Cresol | | | | | |
| 5° C. | 2.46 mg/ml | 0.98 mg/ml | 0.05% | 0.24% | 0.87% |
| 30° C. | 2.45 mg/ml | 0.98 mg/ml | 0.05% | 0.24% | 0.87% |
| 40° C. | 2.45 mg/ml | 0.98 mg/ml | 0.06% | 0.24% | 0.88% |
| Benzyl Alcohol | | | | | |
| 5° C. | 10.1 mg/ml | 0.98 mg/ml | 0.05% | 0.25% | 0.11% |
| 30° C. | 10.1 mg/ml | 0.98 mg/ml | 0.05% | 0.25% | 0.11% |
| 40° C. | 9.8 mg/ml | 0.96 mg/ml | 0.05% | 0.24% | 0.11% |

TABLE 4

Stability of Meta-Cresol Formulation to Autoclaving

| Autoclave Cycle | Meta-Cresol Content | Granisetron | degradation product 1 | degradation product 2 | degradation product 3 |
|---|---|---|---|---|---|
| before autoclaving | 2.46 mg/ml | 0.98 mg/ml | 0.02% | 0.19% | 0.05% |
| 15 mins | 2.40 mg/ml | .96 mg/ml | 0.05% | 0.25% | 0.53% |
| 60 mins | 2.40 mg/ml | 0.96 mg/ml | 0.05% | 0.28% | 0.93% |

EXAMPLE 5

Preservative Efficacy Testing

The target pH of the multidose vial is 6 and limits of 5 to 7. The literature suggests that efficacy of benzyl alcohol decreases with increasing pH above pH5. Efficacy of the preservative was therefore assessed over the lower pH range 4 to 6. Vials prepared at pH4, 5 and 6 were tested for preservative efficacy according to the USP XXII 1990—"Antimicrobial Preservative Effectiveness.

For bacteria, the acceptance criteria require that the number of organisms per mL is reduced by a factor of not less than $10^3$ in 14 days and there is no increase thereafter. All three batches met these criteria for *P aeruginosa*, *S. aureus* and *E. coli*.

For yeasts and molds, the acceptance criterion requires that the number of organisms does not increase throughout the 28 day test period. All three batches met this criterion for *C. albicans* and *A. niger*.

In summary, vials prepared at pH4, 5 and 6 all pass the USP test for preservative efficacy.

EXAMPLE 6

Accelerated Stability Testing

Accelerated stability testing was performed to assess the compatibility of the final formulation with the commercial packaging components and to provide an indication of the stability of the product. Vials were placed on store in both upright and inverted positions to assess compatibility with the stoppers.

Results of the stability testing are provided in Table 5. The benzyl alcohol content remained unchanged from initial in both upright and inverted vials at all conditions. No loss of endo-N-(9-methyl-9-azabicyclo[3.3.1.]non-3-yl)-1-methyl-1H-indazole-3-carboxamide hydrochloride or increase in degradation productions were observed. The results confirm that the formulation is compatible with the packaging components and indicate good product stability.

TABLE 5

Compatibility of Selected Formulation with Packaging Components

| Storage condition | Benzyl Alcohol (mg/mL) | Granisetron (mg/mL) | degradation product 1 (% w/w) | degradation product 2 (% w/w) | degradation product 3 (% w/w) |
|---|---|---|---|---|---|
| Initial | 10.1 | 0.99 | 0.06 | 0.23 | 0.07 |
| 5° C. upr | 10.0 | 0.99 | 0.05 | 0.21 | 0.05 |
| 5° C. inv | 9.9 | 0.98 | 0.05 | 0.21 | 0.05 |
| 30° C. upr | 10.0 | 0.99 | 0.04 | 0.21 | 0.05 |
| 30° C. inv | 10.1 | 0.98 | 0.05 | 0.21 | 0.05 |
| 40° C. upr | 10.0 | 0.99 | 0.05 | 0.21 | 0.05 |
| 40° C. inv | 10.0 | 0.99 | 0.05 | 0.21 | 0.05 | upr = upright
inv = inverted

EXAMPLE 7

Stability and Preservative Efficacy During Use

The experiment was conducted using endo-N-(9-methyl-9-azabicyclo[3.3.1.]non-3-yl)-1-methyl-1H-indazole-3-carboxamide hydrochloride 4.48 mg/4 mL vials containing 4×1.12 mg/1 mL doses of endo-N-(9-methyl-9-azabicyclo[3.3.1.]non-3-yl)-1-methyl-1H-indazole-3-carboxamide hydrochloride. Antimicrobial preservative efficacy testing on the full vials showed that 1% w/w benzyl alcohol was efficacious at the time of manufacture. However, with each successive removal of a dose, the vial contents are potentially contaminated and the headspace in the vial is increased. In order to determine the duration of stability (or use-by date from opening) the following was employed.

Three 1 mL aliquots were withdrawn from the vials in immediate succession then the vials containing the residual solution were stored for 35 days. This procedure tested the worst case scenario wherein the vial contents are subjected to the highest potential microbial challenge and exposed to the largest headspace. After 35 days the vials were test indicated no change in benzyl alcohol content or endo-N-(9-methyl-9-azabicyclo[3.3.1.]non-3-yl)-1-methyl-1H-indazole-3-carboxamide hydrochloride content. The solution was found to be chemically stable throughout the testing period.

Results of USP Antimicrobial Preservative Efficacy test found that, for bacteria, the number of organisms recovered per mL was reduced by a factor of greater than $10^3$ within 14 days of the challenge and there was no increase thereafter. For molds and yeast there was no increase in the number of organisms throughout the testing period. The partially used vials therefore passed the USP Antimicrobial Preservative Efficacy test. This experiment demonstrated that the solution remained stable and preserved for a period of at least 35 days.

While the preferred embodiments of the invention are illustrated by the above, it is to be understood that the invention is not limited to the precise instructions herein disclosed and that the right to all modifications corning within the scope of the following claims is reserved.

What is claimed is:

1. A multidose aqueous formulation comprising endo-N-(9-methyl-9-azabicyclo[3.3.1]non-3-yl)-1-methyl-1H-indazole-3-carboxamide hydrochloride and as a preservative, benzyl alcohol.

2. A multidose aqueous formulation as disclosed in claim 1, further comprising citric acid.

3. A multidose aqueous formulation as disclosed in claim 1 wherein benzyl alcohol is present in an amount from about 0.85% to about 1.15% w/w.

4. A multidose aqueous formulation as disclosed in claim 2 wherein benzyl alcohol is present in an amount from about 0.85% to about 1.15% w/w and citric acid, as citric acid monohydrate, is present in an amount from about 0.15% to about 0.25% w/w.

5. A multidose aqueous formulation as disclosed in claim 3 wherein benzyl alcohol is present in an amount of about 1.0% w/w.

6. A multidose aqueous formulation as disclosed in claim 4 wherein benzyl alcohol is present in an amount of about 1.0% w/w and citric acid, as citric acid monohydrate, is present in an amount of about 0.2% w/w.

7. A 4 mL multidose aqueous formulation as disclosed in claim 4 wherein each 1 mL contains 1.12 mg endo-N-(9-methyl-9-azabicyclo[3.3.1]non-3-yl)-1-methyl-1H-indazole-3-carboxamide hydrochloride, and wherein benzyl alcohol is present in an amount from about 0.85% to about 1.15% w/w and citric acid, as citric acid monohydrate, is present in an amount from 0.15% to 0.25% w/w.

8. A multidose aqueous formulation as disclosed in claim 7 wherein benzyl alcohol is present in an amount of about 10 mg and citric acid is present in an amount of about 2 mg.

9. A multidose aqueous formulation as disclosed in claim 7 wherein the product is stable with regards to bacteria, mold and yeast contamination for a period of at least 35 days from the first aliquot extraction.

10. A multidose aqueous formulation as disclosed in claim 8 wherein the product is stable with regards to bacteria, mold and yeast contamination for a period of at least 35 days from the first aliquot extraction.

* * * * *

UNITED STATES PATENT AND TRADEMARK OFFICE
CERTIFICATE OF CORRECTION

PATENT NO. : 6,294,548 B1
DATED : September 25, 2001
INVENTOR(S) : Susan James

It is certified that error appears in the above-identified patent and that said Letters Patent is hereby corrected as shown below:

<u>Column 8,</u>
Line 17, delete "8" and insert -- 9 --.

Signed and Sealed this

Sixth Day of August, 2002

*Attest:*

*Attesting Officer*

JAMES E. ROGAN
*Director of the United States Patent and Trademark Office*